United States Patent [19] [11] 4,322,428
Matsumoto et al. [45] Mar. 30, 1982

[54] 2(4-FLUOROPHENYL)-4,5,-BIS(4-METHOXYPHENYL)THIAZOLE AND METHOD OF USE

[75] Inventors: Ken Matsumoto; Peter P. K. Ho, both of Indianapolis, Ind.

[73] Assignee: Eli Lilly and Company, Indianapolis, Ind.

[21] Appl. No.: 136,591

[22] Filed: Apr. 2, 1980

[51] Int. Cl.$^3$ ............................................. C07D 277/20
[52] U.S. Cl. ................................. 424/270; 548/202; 548/203
[58] Field of Search ................ 548/202, 203; 424/270

[56] References Cited

U.S. PATENT DOCUMENTS

| | | | |
|---|---|---|---|
| 3,458,526 | 7/1969 | Lednicer | 260/306.8 |
| 3,476,766 | 11/1969 | Brown | 260/302 |
| 3,506,679 | 4/1970 | Cavalla et al. | 260/302 |
| 3,558,644 | 1/1971 | Lednicer | 260/302 |
| 3,560,514 | 2/1971 | Lednicer | 260/302 |
| 4,168,315 | 9/1979 | Rynbrandt et al. | 424/270 |
| 4,197,306 | 4/1980 | Harrison et al. | 548/202 |

FOREIGN PATENT DOCUMENTS 5219 11/1979 European Pat. Off. .

OTHER PUBLICATIONS

CA 73 3835u, (1970).
CA 77 139031u, (1972).
CA 77 19577e, (1972).
CA 80 70743y, (1974).
Bullet. de la Société Chimque de France, (1967), 12, 4523-4533.
CA 56 8719u, (1962).

Primary Examiner—Nicholas S. Rizzo
Attorney, Agent, or Firm—Karen B. O'Connor; Arthur R. Whale

[57] ABSTRACT

Novel triaryl thiazole compounds are useful as analgesic agents. In particular, 2-(4-halophenyl)-4,5-bis(4-methoxyphenyl)thiazoles are used. These compounds are prepared by condensation of a substituted thiobenzamide with a substituted desyl chloride.

15 Claims, No Drawings

2(4-FLUOROPHENYL)-4,5,-BIS(4-METHOXYPHENYL)THIAZOLE AND METHOD OF USE

BACKGROUND OF THE INVENTION

It is an object of this invention to provide novel triarylthiazole compounds. These compounds exhibit pharmacological activity as prostaglandin synthetase inhibitors, analgesic agents, anti-inflammatory agents, antiarthritic agents, antipyretic agents, and antithrombotic agents.

Certain diarylthiazole compounds are useful as antiinflammatory agents. In U.S. Pat. No. 3,476,766, Brown describes the use of 2,4-diarylthiazoles, which are substituted at the 5-position with carboxylic acid or acid derivatives, as anti-inflammatory agents. Anti-inflammatory activity is also taught for 2,5- and 4,5-diarylthiazoles, which are substituted at the 2- or 4-position with an aliphatic acid radical, in U.S. Pat. No. 3,506,679. Three patents (U.S. Pat. Nos. 3,458,526; 3,558,644; and 3,560,514) discuss the use of 2-substituted-4,5-bis(4-methoxyphenyl)thiazoles as anti-inflammatory agents.

Diarylthiazole compounds can also be useful as antithrombotic agents as shown in U.S. Pat. No. 4,168,315. Particularly, 4,5-bis(4-methoxyphenyl)thiazoles are described as useful in reducing platelet aggregation.

Some triarylthiazole compounds are discussed in the literature, but no utilities are described for these compounds. Known triarylthiazole compounds include 2,5-bis(4-fluorophenyl)-4-phenylthiazole; 2-(4-nitrophenyl)-4,5-bis(phenyl)thiazole; triphenylthiazole; and 2-phenyl-4,5-bis(4-chlorophenyl)thiazole.

Triarylimidazole compounds, such as 2-(4-fluorophenyl)-4,5-bis(4-methoxyphenyl)imidazole, are disclosed in European Patent application No. 5,219 as analgesic agents, anti-inflammatory agents, antipyretic agents, prostaglandin synthetase inhibitors, and thrombocyte aggregation inhibitors.

Triaryloxazole compounds are described in CA 56:8719d as light protecting agents, and optical brighteners.

SUMMARY OF THE INVENTION

This invention describes compounds of the formula I

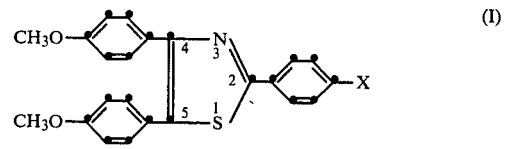

(I)

wherein

X is hydrogen, bromo, chloro or fluoro.

These compounds are useful as prostaglandin synthetase inhibitors, analgesic agents, anti-inflammatory agents, anti-arthritic agents, antipyretic agents, and antithrombotic agents. These compounds are especially useful as analgesic agents. Another aspect of this invention is a pharmaceutical formulation comprising an effective amount of a compound of the formula I in combination with a pharmaceutically-acceptable vehicle.

DETAILED DESCRIPTION OF THE INVENTION

The compounds of this invention are of the formula I and are as follows:

2-phenyl-4,5-bis(4-methoxyphenyl)thiazole;

2-(4-bromophenyl)-4,5-bis(4-methoxyphenyl)thiazole;

2-(4-chlorophenyl)-4,5-bis(4-methoxyphenyl)thiazole; and 2-(4-fluorophenyl)-4,5-bis(4-methoxyphenyl)thiazole. The preferred compound is 2-(4-fluorophenyl)-4,5-bis(4-methoxyphenyl)thiazole.

The triarylthiazole compounds of this invention are generally prepared by the following reaction scheme:

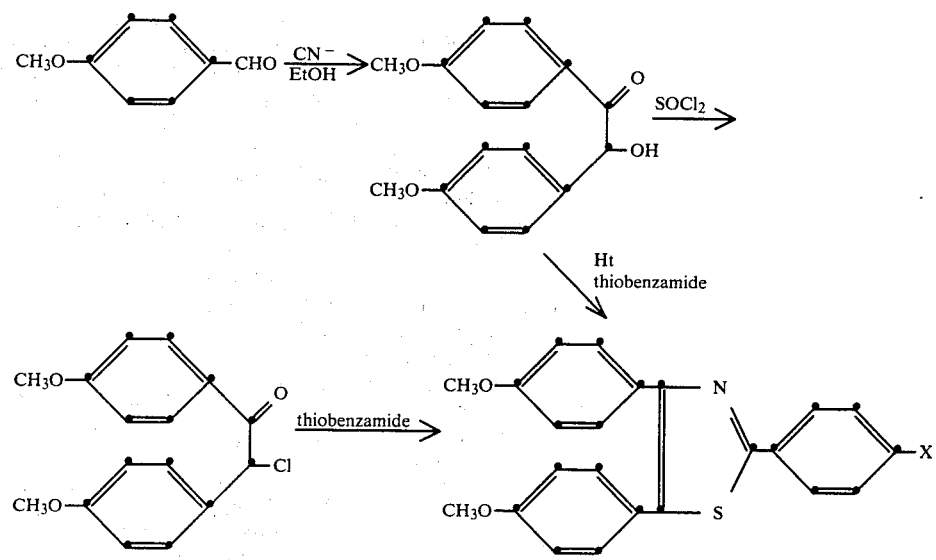

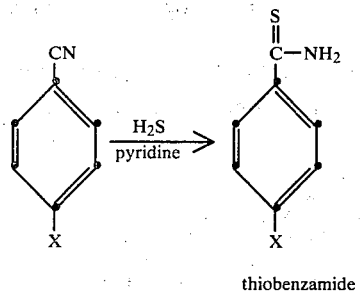

thiobenzamide

A p-methoxybenzaldehyde is reacted with an alkali metal cyanide in an alcohol solution to form the corresponding dimethoxy-substituted benzoin. Typical alcohols include ethanol, methanol, butanol, isopropanol, t-butanol, and the like, with ethanol preferred. This reaction, called the Benzoin condensation, can be found in *Organic Reactions* 4, 269 (1948).

The dimethoxy substituted benzoin (anisoin) is then chlorinated by thionyl chloride, phosphorus pentachloride, or phosphorus trichloride, resulting in a substituted desyl chloride (2-chloro-2-phenylacetophenone). In this reaction, the presence of a base, such as pyridine, 2,6-lutidine, or triethylamine, is preferred, but not necessary. Instead, the reaction can proceed in a solvent like benzene, toluene, tetrahydrofuran, chloroform, etc. or in both a solvent and base. Typical reaction temperatures vary from about 0° C. to about 150° C., with the preferred temperature being about 50° C. Typical reaction times are from about two to four hours.

The thiobenzamide used in the condensation with the desyl chloride can be prepared by two methods. The first is the reaction of the corresponding nitrile with hydrogen sulfide in the presence of a strong base, such as triethylamine, trimethylamine, tripropylamine, N-methylpyrrolidine, and N-methylpiperidine. The preferred base is triethylamine. Typical solvents include pyridine, 2,6-lutidine, chloroform, tetrahydrofuran, methylene chloride, toluene, xylene, and the like, with the preferred solvent being pyridine. The reaction can be run from about room temperature to about 300° C., depending upon the nature of the reactants.

The second method of preparing thiobenzamides is the reaction of the nitrile compound with a source of hydrogen sulfide in the presence of a proton source and heat. Thioacetamide, thiopropionamide, thiobutyramide, thiobenzamide, and the like can serve as a source of hydrogen sulfide, but thioacetamide is preferred. At least a molar amount of thioacetamide is necessary, although an excess can be used. Proton sources include acids such as hydrochloric acid, hydrobromic acid, hydroiodic acid, p-toluenesulfonic acid, methanesulfonic acid, trifluoroacetic acid, and the like. This reaction is run in such solvents as dimethylformamide, dimethylsulfoxide, tetrahydrofuran, chloroform, toluene, and the like at temperatures from about 25° C. to about 100° C.

The condensation of the substituted thiobenzamide with the substituted desyl chloride is carried out in a solvent, such as dioxane, tetrahydrofuran, ethanol, dimethylformamide, dimethylsulfoxide, benzene, toluene, chloroform, methylene chloride and ether. Preferred solvents are dioxane, tetrahydrofuran, ethanol, and toluene. The condensation can be run at temperatures from about 20° C. to about 150° C., with the preferred temperature being about 100° C. Heating time varies with the temperature used, but a preferable time is between two and three hours.

The compounds of this invention can also be formed from the substituted benzoin compound without forming the desyl chloride, by reacting the benzoin directly with a substituted thiobenzamide using an acid catalyst. Typical acids include sulfuric, hydrochloric, hydrobromic, hydroiodic, p-toluenesulfonic, trifluoroacetic, or similarly strong acids. The reaction is run in a solvent such as dioxane, toluene, tetrahydrofuran, chloroform, benzene, or xylene, preferably dioxane or toluene. The temperature can range from about 20° C. to about 150° C.; the preferred temperature is between about 60° C. and about 150° C. The time of reaction can be from several hours to several days; however, shorter reaction times are preferred.

The preparation of the thiazole compounds of this invention are described in the following examples. The examples are illustrative of the compounds embraced by the invention and of the methods commonly employed in their preparation, but are not to be construed as limiting the invention.

EXAMPLE 1

4,4'-Dimethoxydesyl chloride

One hundred grams (0.37 mole) of anisoin and 45 ml (0.55 mole) of pyridine were placed in a beaker and heated until the anisoin was completely in solution. After cooling the beaker in an ice bath, a solid was formed. This solid was broken up and then 36 ml (0.50 mole) of thionyl chloride was added with stirring, forming a liquid mixture. After 1 hr, 250 ml water was added and the organic materials extracted with ether, washed with water, dried over $Na_2SO_4$ and evaporated to afford a crude oil. Most of the oil was taken up in ether and a residual solid was filtered away. Cooling resulted in a yellow-brown solid which was filtered and collected. Recrystallization again from ether yielded 37.9 g (36%) of a solid. The product had a melting point of about 80°–81° C.

NMR spectrum (deuterated chloroform) showed the following:

$\delta$ (ppm) = 3.80, 3.82, singlet (6H) methoxys
= 6.30 singlet (1H) methine
= 7.40 multiplet (8H) phenyls The following elemental analysis was obtained:
Calculated for $C_{16}H_{15}ClO_3$:
Theory: C, 66.10; H, 5.20; Cl, 12.19. Found: C, 66.33; H, 5.49; Cl, 12.22.

EXAMPLE 2

4-Fluorothiobenzamide

One hundred grams (0.826 mole) of 4-fluorobenzonitrile was dissolved in 500 ml. of pyridine and 116 ml. of triethylamine. A stream of hydrogen sulfide was bubbled through the solution at room temperature for about 3.5 hours, then the mixture was poured onto ice-water. A yellow solid was obtained and filtered, then it was dried at 65° C. under a vacuum. The product obtained had a melting point of about 145°–147° C. and weighed 107.5 g. (84% yield).

The following elemental analysis was obtained:
Calculated for $C_7H_6FNS$:
Theory: C, 54.18; H, 3.90; N, 9.03. Found: C, 53.95; H, 4.10; N, 9.22.

EXAMPLE 3

Thiobenzamide

Following the procedure in Example 2, thiobenzamide was prepared using 103 g. (1.0 mole) benzonitrile as the starting material. The product had a melting point of about 114.5°–117° C. and weighed 74.4 g. (54% yield). The mass spectrum showed the expected molecular ion at (mass to charge) m/e=137.

The following elemental analysis was obtained:
Calculated for $C_7H_7NS$:
Theory: C, 61.28; H, 5.14; N, 10.21. Found: C, 61.43; H, 5.44; N, 10.48.

EXAMPLE 4

4-Chlorothiobenzamide

Following the procedure in Example 2, 4-chlorothiobenzamide was prepared using 25 g. (0.187 mole) 4-chlorobenzonitrile as the starting material. The product had a melting point of about 128°–130.5° C. and weighed 15.4 g. (48% yield). The mass spectrum showed the expected molecular ion at m/e=171.

The following elemental analysis was obtained:
Calculated for $C_7H_6ClNS$:
Theory: C, 48.98; H, 3.52; N, 8.16. Found: C, 49.02; H, 3.54; N, 8.30.

EXAMPLE 5

4-Bromothiobenzamide

Following the procedure in Example 2, 4-bromothiobenzamide was prepared using 25 g. (0.137 mole) 4-bromobenzonitrile as the starting material. The product had a melting point of about 142°–144° C. and weighed 15.8 g. (53% yield). The mass spectrum showed the expected molecular ions at m/e=215 and 217.

The following elemental analysis was obtained:
Calculated for $C_7H_6BrNS$:
Theory: C, 38.91; H, 2.80; N, 6.48. Found: C, 39.16; H, 2.90; N, 6.24.

EXAMPLE 6

2-(4-Bromophenyl)-4,5-bis(4-methoxyphenyl)thiazole

Fifty ml. of dioxane was used to dissolve 7.43 g. (0.034 mole) of 4-bromothiobenzamide with heating to about 60° C. Then 10.0 g. (0.034 mole) of 4,4'-dimethoxydesyl chloride in 50 ml. of dioxane was added and the mixture was heated to 100° C. for two hours. The mixture was cooled and acidified with 1 N hydrochloric acid. Most of the dioxane was removed in vacuo and the solid formed was filtered. The solid was purified by silica gel chromatography (400 g.), using benzene as the eluting agent. The product had a melting point of about 155°–157° C. and weighed 8.83 g. (57% yield). The mass spectrum showed the expected molecular ions at m/e=451 and 453.

The NMR spectrum (deuterated chloroform) showed the following:

$\delta$ (ppm) = 3.80 singlet (6H) methoxys
= 7.40 multiplet (12H) phenyls

The following elemental analysis was obtained:
Calculated for $C_{23}H_{18}BrNO_2S$:
Theory: C, 61.07; H, 4.01; N, 3.10; S, 7.09; Br 17.66. Found: C, 61.32; H, 3.71; N, 3.27; S, 7.00; Br 17.90.

EXAMPLE 7

2-(4-Fluorophenyl)-4,5-bis(4-methoxyphenyl)thiazole

Following the procedure in Example 6, 2-(4-fluorophenyl)-4,5-bis(4-methoxyphenyl)thiazole was prepared using 5.34 g. (0.034 mole) 4-fluorothiobenzamide and 10.0 g. (0.034 mole) 4,4'-dimethoxydesyl chloride as the starting materials. The product had a melting point of about 140°–142° C. and weighed 6.74 g. (50% yield) after silica gel chromatography. The mass spectrum showed the expected molecular ion at m/e=391.

The NMR spectrum (deuterated chloroform) showed the following:

$\delta$ (ppm) = 3.80 singlet (6H) methoxys
= 7.30 multiplet (12H) phenyls

The following elemental analysis was obtained:
Calculated for $C_{23}H_{18}FNO_2S$:
Theory: C, 70.57; H, 4.63; F, 4.85; N, 3.58; S, 8.19. Found: C, 70.48; H, 4.41; F, 5.05; N, 3.44; S, 8.09.

EXAMPLE 8

2-(4-Chlorophenyl)-4,5-bis(4-methoxyphenyl)thiazole

Following the procedure of Example 6, 2-(4-chlorophenyl)-4,5-bis(4-methoxyphenyl)thiazole was prepared using 5.90 g. (0.034 mole) 4-chlorothiobenzamide and 10.0 g. (0.034 mole) 4,4'-dimethoxydesyl chloride as the starting materials and an ethanol-sodium acetate mixture as the solvent. The solution also contained a catalytic amount of piperidine and was refluxed for about 16 hours.

After silica gel chromatography, the product weighed 5.4 g. (38% yield) and had a melting point of about 134°–137° C. The mass spectrum showed the expected molecular ions at m/e=407 and 409.

The following elemental analysis was obtained:
Calculated for $C_{23}H_{18}ClNO_2S$:
Theory: C, 67.72; H, 4.45; N, 3.43. Found: C, 67.59; H, 4.73; N, 3.43.

EXAMPLE 9

2-(4-Fluorophenyl)-4,5-bis(4-methoxyphenyl)thiazole

Three ml. of concentrated sulfuric acid, 250 ml. of dioxane, 27.2 g. (0.10 mole) of anisoin, and 15.5 g. (0.10 mole) of 4-fluorothiobenzamide were placed in a round bottom flask. The mixture was stirred at reflux for 3 days, then cooled to room temperature, and poured onto ice. Then the mixture was extracted with ethyl acetate, washed with water, and dried over sodium sulfate. After the ethyl acetate was evaporated, a crude solid of 35 g. remained. The solid was then recrystallized from ethyl acetate and weighed 27.5 g. (70% yield). It had a melting point of about 140°–141.5° C. and the mass spectrum showed the expected molecular ion at m/e=391.

The NMR spectrum (deuterated chloroform) showed the following:

$\delta$ (ppm) = 3.80 singlet (6H) methoxys
= 7.40 multiplet (12H) phenyls

The following elemental analysis was obtained:
Calculated for $C_{23}H_{18}FNO_2S$:
Theory: C, 70.57; H, 4.63; N, 3.58.
Found: C, 70.34; H, 5.04; N, 3.88.

EXAMPLE 10

2-Phenyl-4,5-bis(4-methoxyphenyl)thiazole

Following the procedure of Example 9, 2-phenyl-4,5-bis(4-methoxyphenyl)thiazole was prepared using 25 g. (0.18 mole) thiobenzamide as a starting material, toluene as the solvent, and p-toluenesulfonic acid as the catalyst. The product weighed 47.7 g. (70% yield) and had a melting point of about 117°–118° C.

The following elemental analysis was obtained:
Calculated for $C_{23}H_{19}NO_2S$:
Theory: C, 73.97; H, 5.13; N, 3.75; S, 8.59. Found: C, 73.87; H, 4.95; N, 3.80; S, 8.79.

The compounds of formula I are effective analgesic agents as demonstrated in the mouse-writhing test, using Cox standard strain albino male mice. An intraperitoneal injection of 0.55% (55 mg/kg.) acetic acid induces writhing in the mice, which is characterized by contraction of the abdominal musculature, extension of the hindlegs, and rotation of the trunk. The compounds were administered in a corn oil-acacia emulsion. The number of writhes is counted for both the control and treated animals and the percent inhibition computed as follows:

$$\% \text{ Inhibition} = 100 - \frac{\text{treated total No. of writhes}}{\text{control total No. of writhes}} \times 100$$

Table I summarizes the mouse-writhing test results. All dosages were given orally (p.o.) and are expressed in mg/kg. The term "$ED_{50}$" means an effective dosage needed to inhibit 50% of the writhing.

TABLE I

| Analgesic Mouse-Writhing Test Results | |
|---|---|
| Compound | $ED_{50}$ mg/kg p.o. |
| 2-Phenyl-4,5-bis(4-methoxyphenyl)thiazole | 2.30 |
| 2-(4-Bromophenyl)-4,5-bis(4-methoxyphenyl)thiazole | 1.46 |
| 2-(4-Chlorophenyl)-4,5-bis(4-methoxyphenyl)thiazole | 3.75 |
| 2-(4-Fluorophenyl)-4,5-bis(4-methoxyphenyl)thiazole | 0.82 |

The compound dosage for humans and animals depends upon the condition of the subject and the analgesic effect desired. Accordingly, a preferred formulation is a pharmaceutical preparation, which is in a suitable unit dosage form to obtain an analgesic effect, comprising, per dosage unit, an effective amount of one or more of the thiazole compounds. Such an effective amount ranges from about 0.5 mg/kg. to about 50 mg/kg.

The oral absorption of the novel thiazole compounds in animals is greatly enhanced by administering the thiazole compounds of formula I in a lipid-containing vehicle. Lipid vehicles include oils, oil-emulsions, sterol esters, waxes, vitamin A esters, and the like.

Still further, lipid vehicles include vegetable oils, such as corn oil, coconut oil, and safflower oil; animal fats, such as lard and spermaceti; phospholipids; and synthetic triglycerides, such as Medium Chain Triglycerides (MCT-$C_8$–$C_{10}$ chain), Long Chain Triglycerides (LCT-$C_{16}$–$C_{18}$ chain).

Excipients can also be added and include glycols, such as polyethylene glycol and polypropylene glycol; cellulose; starch; and the like.

Although oil alone can be used to administer the thiazole compound if the animal receiving the thiazole-oil mixture can rapidly digest and absorb the oil, an oil emulsion is the preferred method of administration. The preferred oil-emulsion is a corn oil-acacia emulsion, formed by dissolving the thiazole compound in corn oil and then emulsifying the thiazole-corn oil mixture with a ten percent acacia solution.

Other emulsifiers or emulsifying agents can include natural emulsifiers, such as acacia; phospholipids, such as lecithin, gelatin, and cholesterol; and synthetic emulsifiers, such as glyceryl esters, like glyceryl monostearate; sorbitan fatty acid esters, like sorbitan monopalmitate (Span 40); polyoxyethylene sorbitan fatty acid esters, like polyoxyethylene sorbitan monopalmitate (Tween 40), and polyoxyethylene sorbitan monoleate (Tween 80); and polyoxyethylene glycol esters, like polyoxyethylene glycol monostearate.

Other methods of administration include fluid or solid unit dosage forms, such as capsules, slurries, suspensions, and the like. For example, one form is a hard gelatin capsule containing the thiazole compound dissolved in fat. First, the compound is dissolved in the fat, while the fat is in a liquid state, then the thiazole-fat mixture is solidified, resulting in a homogenous amorphous solid solution. The mixture is then pulverized and placed in a hard gelatin capsule. An emulsifier can also be added to the fat-thiazole mixture, if desired.

Alternatively, fluid unit dosage forms, such as soft gelatin capsules, can be used to administer the thiazole compounds. These capsules are prepared by machine encapsulation of a slurry of the thiazole compound and an acceptable lipid vehicle. A slurry alone with out encapsulation can also be administered.

Still another fluid unit dosage form is a suspension, which is prepared with a syrup vehicle aided by a suspending agent, such as acacia, tragacanth, methylcellulose and the like.

A further method of administration is to orally administer the thiazole compound to an animal previously fed a fatty meal, thereby using the fats consumed in the meal as the lipid-containing vehicles. Before the thiazole compound is administered to the animal, the compound is micronized and coated with a surfactant, such as acacia.

Therefore, one aspect of this invention is a pharmaceutical formulation comprising an effective amount of a compound of formula I in combination with a pharmaceutically-acceptable lipid-containing vehicle. A surfactant or emulsifier can also be added to the formulation.

Another aspect of this invention is a pharmaceutical formulation comprising an effective amount of a compound of formula I in combination with a pharmaceutically-acceptable surfactant-containing vehicle. This formulation is administered with or after the animal has a fatty meal.

We claim:
1. The compound 2-(4-fluorophenyl)-4,5-bis(4-methoxyphenyl)thiazole.
2. A method of treating pain, which comprises administering to a warm-blooded animal in need of such treatment, an analgesically-effective amount of a compound of the formula II

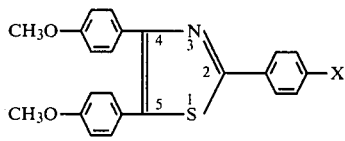
(II)

wherein
X is hydrogen, bromo, chloro, or fluoro.
3. The method of claim 2 wherein the compound is 2-phenyl-4,5-bis(4-methoxyphenyl)thiazole.
4. The method of claim 2 wherein the compound is 2-(4-bromophenyl)-4,5-bis(4-methoxyphenyl)thiazole.
5. The method of claim 2 wherein the compound is 2-(4-chlorophenyl)-4,5-bis(4-methoxyphenyl)thiazole.
6. The method of claim 2 wherein the compound is 2-(4-fluorophenyl)-4,5-bis(4-methoxyphenyl)thiazole.
7. A pharmaceutical formulation useful in the treatment of pain comprising an analgesically-effective amount of a compound of the formula II

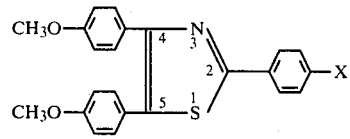
(II)

wherein
X is hydrogen, bromo, chloro, or fluoro in combination with a pharmaceutically-acceptable lipid-containing vehicle.
8. The formulation of claim 7 wherein the formulation also contains a pharmaceutically-acceptable surfactant.
9. The formulation of claim 8 wherein the lipid-containing vehicle is an oil emulsion.
10. The formulation of claim 9 wherein the oil emulsion comprises corn oil and acacia.
11. The formulation of claim 10 wherein the compound is 2-(4-fluorophenyl)-4,5-bis(4-methoxyphenyl)-thiazole.
12. The formulation of claim 10 wherein the compound is 2-(4-bromophenyl)-4,5-bis(4-methoxyphenyl)-thiazole.
13. The formulation of claim 10 wherein the compound is 2-(4-chlorophenyl)-4-5-bis(4-methoxyphenyl)-thiazole.
14. The formulation of claim 10 wherein the compound is 2-phenyl-4,5-bis(4-methoxyphenyl)thiazole.
15. A pharmaceutical formulation useful in the treatment of pain comprising an analgesically-effective amount of a compound of the formula II

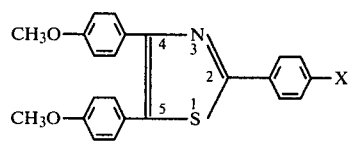
(II)

wherein
X is hydrogen, bromo, chloro, or fluoro in combination with a pharmaceutically-acceptable surfactant-containing vehicle.

* * * * *